United States Patent [19]

Weeks et al.

[11] Patent Number: 5,879,946
[45] Date of Patent: Mar. 9, 1999

[54] MONITORING OF CHEMICAL ADDITIVES

[75] Inventors: Ian Weeks; Sian Aerona Herbert, both of Cardiff, Wales

[73] Assignee: Molecular Light Technology Limited, Cardiff, United Kingdom

[21] Appl. No.: 842,118

[22] Filed: Apr. 28, 1997

Related U.S. Application Data

[63] Continuation of Ser. No. 277,864, Jul. 20, 1994, abandoned.

[30] Foreign Application Priority Data

Jul. 21, 1993 [GB] United Kingdom ................ 9315129.8

[51] Int. Cl.$^6$ .................................................. G01N 21/76
[52] U.S. Cl. ................................ 436/60; 422/52; 436/56; 436/164; 436/172; 250/361 C; 250/259; 250/302
[58] Field of Search .............................. 422/52; 436/56, 436/60, 164, 172; 250/361 C, 302, 259

[56] References Cited

U.S. PATENT DOCUMENTS

| | | | |
|---|---|---|---|
| 4,419,452 | 12/1983 | Imai et al. ................................. | 436/89 |
| 4,793,977 | 12/1988 | Norris ....................................... | 422/55 |
| 4,927,769 | 5/1990 | Chang et al. ............................ | 436/518 |
| 5,470,754 | 11/1995 | Rounbehler et al. .................... | 436/106 |
| 5,643,728 | 7/1997 | Slater et al. ............................... | 435/6 |

FOREIGN PATENT DOCUMENTS

| | | |
|---|---|---|
| 0327163 | 8/1989 | European Pat. Off. . |
| 0512404A1 | 11/1992 | European Pat. Off. . |

OTHER PUBLICATIONS

Fleschka et al. Quantitative Analytical Chemistry, 2nd Edition, p. 478, 1982.

Sax et al. Hawley's Condensed Chemical Dictionary, 11th Edition, p. 17, 1987.

*Primary Examiner*—Jill Warden
*Assistant Examiner*—Sharidan Carrillo

[57] ABSTRACT

A method for allowing authentification of a bulk liquid e.g. petrol or another mineral oil based product, comprises introducing into the liquid a small amount of a chemiluminescent substance. Samples for authentification are subjected to the conditions required to trigger the chemiluminescent reaction and monitored for chemiluminescent emission.

13 Claims, No Drawings

MONITORING OF CHEMICAL ADDITIVES

This is a continuation of application Ser. No. 08/277,864 filed on Jul. 20, 1994, now abandoned.

BACKGROUND OF THE INVENTION

This invention relates to a method for monitoring the levels of chemical marker compounds and an assay kit enabling the monitoring to be carried out under field or laboratory conditions. The invention is particularly, but not exclusively, directed towards the detection of added chemicals in liquid products, especially in oil based products such as petroleum.

Chemical additives are important constituents of oil based products such as petroleum, diesel oil and lubricating oils. The additives are generally designed to impart favourable and occasionally unique properties to the product such that their absence or a reduction in their concentration may result in a significant loss of performance. These additives are normally introduced at a central distribution point into products which may be distributed on a world wide basis. Since product performance is dependent on the presence of appropriate levels of the additives in the final product as it is retailed, a system for demonstrating their presence at any point in the distribution chain is required.

A second, but equally important consideration, relates to the problem of counterfeiting. Products which are perceived to have favourable properties over rival products will be imitated for reasons of commercial gain. They may not, for example, enjoy the benefits of the correct additives but may be sold as to imitate visually the better product. In such a situation, the ability to distinguish the genuine product from imitations is highly desirable.

Accurate identification of oil based products is also important since litigation can be brought as a consequence of accidents and spillages. In these situations, the presence of a marker substance which can identify or alternatively exclude a particular manufacturer or distributor can be of extreme value.

In summary, the presence of readily identifiable marker substances in oil based products could contribute significantly to several aspects of quality assurance in the oil and petroleum industry. Up to now, it appears that no simple procedure has yet been devised to provide such a system.

Fuel additives are frequently beneficial to the performance of the product at extremely low concentrations. However, their incorporation into fuels at such low concentrations means that they are not readily detected by conventional analytical procedures. Even in situations where the additive can be detected by sophisticated physical/chemical techniques, there is the problem that samples must be taken to a central laboratory for analysis which may be tedious and time consuming.

One recent approach has been to make use of the fact that many organic compounds are immunogenic so that immunological assay methods can be applied to their detection (see for example EP-A-0327163). Though these methods do possess inherently high sensitivities, they are not intrinsically simple to perform and therefore do not lend themselves to analysis in the field. Moreover, they involve the use of monoclonal antibodies which may lack the stability of simple chemicals, again restricting the site or scope of application. This approach relies on subjecting a small sample to an assay procedure to quantify the additive compound of interest; there is no suggestion of introducing a chemical marker to the bulk product or along the distribution chain at source which is subsequently triggered possibly many weeks later several steps down the distribution chain to allow analysis or detection thereof.

We have developed a radically different approach which uses an independent substance which has some unique, easily detected property and which can be added to the fuel at source or along the distribution chain as a marker along with the additives. The marker should possess certain characteristics. Firstly, it should partition into the organic phase so that contact with water, as might occur for example in a storage vessel, will not cause substantial partitioning into the aqueous phase. Secondly, the marker compound should remain stable in the fuel for several weeks without substantial alteration of its detection characteristics. Thirdly, the marker compound should be reproducibly detectable at extremely low concentrations, partly for reasons of cost but also to ensure that it does not itself interfere with the performance of the fuel. The marker compound should be detectable quantitatively with a simple detection system. Finally, neither the fuel itself or any other additive should interfere significantly with the behaviour of the marker under normal analytical conditions.

SUMMARY OF THE INVENTION

Accordingly, in one aspect of this invention, there is provided a method for allowing authentication of a bulk liquid, which comprises introducing into said bulk liquid a chemiluminescent substance capable of taking part in a chemiluminescent reaction, exposing samples for authentication to the conditions required to trigger said chemiluminescence reaction, and monitoring whether said reaction occurs.

Chemiluminescent compounds have the property that, under defined conditions, they can be induced to emit light. This process can involve activation of a reaction by the supply of heat to the compound or alternatively may involve a simple chemical triggering mechanism. The light emission can be detected or quantified using a simple photon counting device. One potential advantage of chemiluminescence is that, generally, endogenous chemiluminescence is low so that a small signal can be readily detected against a very low background.

The term "bulk liquid" is used to define any liquid to be authenticated. Whilst primarily intended to cover industrial liquids such as mineral oils intended to be supplied in large volumes, the term is also intended to embrace liquids supplied in small volumes, other than for analytical purposes. The chemiluminescent substance may be any suitable substance which retains at least some of its chemiluminescence when introduced into said bulk liquid, and includes those chemiluminescent materials referred to as bioluminescent. The terms "chemiluminescent substance" and the like should be interpreted broadly as including chemiluminescent compounds as well as cofactors, catalysts or other substances capable of taking part in a chemiluminescent reaction.

In another aspect, this invention provides a method of detecting subsequent dilution of a sample of bulk liquid which comprises introducing into said undiluted bulk liquid a known amount of a chemiluminescent marker substance, taking a sample of said bulk liquid, initiating the chemiluminescent reaction in said sample, monitoring the characteristics of said reaction, comparing said characteristics with those corresponding to the undiluted bulk liquid, to determine the extent (if any) of dilution of said bulk liquid.

In a further aspect, this invention provides a method of treating a bulk liquid to allow subsequent identification, analysis, or determination of the presence of an additive therein, which comprises introducing into said bulk liquid an amount of a chemiluminescent marker substance indicating the presence of, or related to the amount of, said additive.

Said chemiluminescent marker substance is preferably introduced into said bulk liquid with said additive. The additive may comprise just one or a plurality of additive substances.

The methods of this invention are particularly useful when said bulk liquid is a mineral oil based product, although it may be any industrial or non-industrial liquid.

Thus, the methods of this invention relate to the use of a chemiluminescent marker which can be incorporated into the fuel at sufficiently low concentrations that it does not affect performance, and which can also be reliably detected using a simple analytical kit.

DESCRIPTION OF THE PREFERRED EMBODIMENT

A preferred aspect of the invention involves the use of chemiluminescent acridinium compounds which have inherently high quantum yields and can therefore be detected with extremely high sensitivity. The application of these compounds as labels for substances of biological interest is disclosed in UK-B-2112779.

Somewhat surprisingly, certain acridinium compounds can be detected with high sensitivity in petroleum by means of addition of simple oxidising reagents, the light output being directly proportional to the concentration of acridinium compound in the sample. A critical observation is that a 10 µl sample of petrol yielded no significant chemiluminescence when subjected to the reagents used to generate the light emitting reaction.

The chemiluminescent marker substance is preferably an acridinium compound capable of undergoing a chemiluminescent reaction and of the general formula:

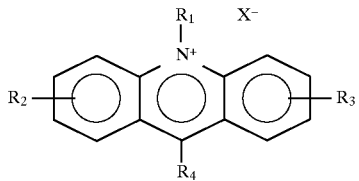

wherein $R_1$ is a moiety capable of being part of a quaternary nitrogen centre, for example an alkyl, alkenyl, alkynyl, alkoxyl or aryl containing group.

$R_2$ and $R_3$ may be the same as $R_1$ or a hydroxyl, carboxyl, amino, substituted amino or halide group, $R_4$ is a moiety whose chemical reactivity permits the compound to undergo a chemiluminescent reaction.

The chemiluminescent marker substance is substantially insoluble in water. Said chemiluminescent marker substance is preferably present in said bulk liquid in an amount between 0.001 ng/µl and 10 ng/µl, and preferably is immunologically unbound in normal use of said bulk liquid.

In another aspect, this invention provides an additive formulation for a bulk liquid, said formulation containing one or more ingredients for modifying or enhancing one or more selected properties of the bulk liquid, in combination with an amount of a chemiluminescent marker substance.

In a further aspect, this invention provides a method of identifying or analysing a bulk liquid to determine the presence or quantity of an additive or other material present in small quantities, the bulk liquid including an amount of a chemiluminescent substance indicating the presence of, or related to the amount of, said additive or other material, which method comprises initiating the chemiluminescent reaction and observing the characteristics of said reaction to determine the presence and/or concentration of said additive or other material.

The observed characteristics may comprise one or more of wavelength, intensity, variation of intensity with time, other kinetic variations, and polarisation.

The invention may make use of other chemiluminescent compounds such as (though not exclusively) phthalhydrazides and their derivatives, phenanthridinium and quinolinium salts, bis-acridinium salts, bis-oxalate esters, dioxetanes and organometallic compounds such as ruthenium chelates. The structures of numerous chemiluminescent compounds are recited in the literature and the selection of suitable compounds in accordance with the detailed criteria contained herein is well within the competance of one skilled in the art.

Our experiments have shown that such compounds may be stored in petroleum for significant periods of time with no loss of chemiluminescent properties. Moreover, we have found that such compounds can be designed so that they will not partition into water should such contamination be present in storage vessels. Finally we have been able to detect as little as 1.2 parts/billion of the acridinium compound in 10 µl of petroleum.

These observations demonstrate that chemiluminescent molecules and in particular acridinium compounds can be used as marker substances in petroleum based products. It is thus possible to add such compounds to petrol at the same time as other, performance related additives are being introduced. Analysis of the amount of chemiluminescent substance at any point in the distribution chain will thus provide an indication such addition has been made and also that the fuel has not been diluted with other base fuel. Moreover, the presence of the chemiluminescent molecule in the fuel will indicate that the fuel is the genuine manufactured material.

In practice, as little as 1 g of a chemiluminescent acridinium derivative can be added to a volume of 1.5 million liters of petroleum and be readily detected after a period of 6 weeks in only 10 µl of fuel. At the concentration of acridinium compound present, there is no detectable effect of the marker on performance. Thus, at this stage, it appears that the use of chemiluminescent markers in fuel offers a simple, reliable and sensitive method for monitoring additive levels.

A further aspect of the invention relates to a test kit for the monitoring of additive levels under field conditions. Luminometers capable of detecting low levels of light emission have been available for several years, though most such instruments are designed for routine laboratory use. Hand held devices have been developed which are capable of reading the light emission from constant sources by means of a photographic plate. In this aspect, the invention provides a luminescence detector including injection devices capable of delivering the reagents necessary to initiate the chemiluminescent reaction. The detector is preferably capable of fitting into a compartment no bigger than a brief case. The light emission is recorded and, if below a certain threshold, will alert the operator to the possibility that the additive level is inadequate. Further tests can then be undertaken in the laboratory to determine the exact nature of the defective level.

The invention will now be further described with reference to the following example:

EXAMPLE

The following compounds (1) and (2) were prepared by standard methods:

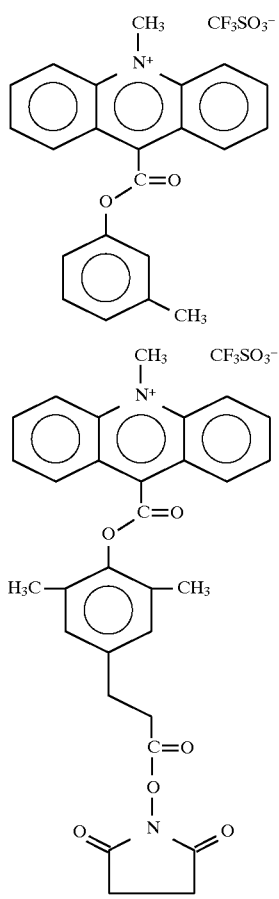

Approximately one hundred μg of each compound were dissolved in 10 ml of dry acetonitrile. Ten μl of each solution were then diluted to a volume of 1 ml with standard unleaded petrol to give a final concentration of acridinium salt of approximately 100 ng/ml. These samples were then stored at room temperature in the dark and, at intervals, 10 μl aliquots of these were removed to measure chemiluminescence. Measurements were carried out in a Berthold "Klinilumat" Luminometer. The chemiluminescent reaction was initiated by injection of 0.3 ml of a solution of 1% hydrogen peroxide In 0.1 M nitric acid followed by 0.3 ml of a solution of 1.0% sodium hydroxide containing 0.2% cetyltrimethylammonium chloride. Luminescence output was integrated over a suitable interval and results obtained after different periods of storage were as follows:

| Time | Light Yield (RLU) |
| --- | --- |
| Compound 1 | |
| Day 1 | $1.5 \times 10^7$ |
| Day 10 | $1.5 \times 10^7$ |
| Day 27 | $1.4 \times 10^7$ |
| Day 33 | $1.3 \times 10^7$ |
| Day 40 | $1.3 \times 10^7$ |
| Compound 2 | |
| Day 1 | $2.4 \times 10^7$ |
| Day 2 | $2.3 \times 10^7$ |
| Day 4 | $2.4 \times 10^7$ |
| Day 10 | $2.5 \times 10^7$ |
| Day 17 | $2.0 \times 10^7$ |

These results show that when either of these compounds is added to standard unleaded petrol, chemiluminescence can be recovered quantitatively within reasonable limits of experimental error over a significant time period.

What is claimed is:

1. A method of authenticating a bulk liquid, which consists of introducing into said bulk liquid a chemiluminescent marker substance capable of taking part in a chemiluminescent reaction, withdrawing a sample of said bulk liquid to be authenticated, exposing said sample to conditions required to trigger a chemiluminescence reaction, determining whether a chemilumninescence reaction occurs, and authenticating said bulk liquid based on whether said chemiluminescence reaction occurs.

2. A method according to claim 1, wherein said bulk liquid is a mineral oil based product.

3. A method according to claim 1, wherein said chemiluminescent marker substance is substantially insoluble in water.

4. A method according to claim 1, wherein said chemiluminescent marker substance is present in said bulk liquid in an amount between 0.001 ng/μl and 10 ng/μl.

5. A method according to claim 1, wherein the chemiluminescent marker substance is immunologically unbound in said bulk liquid.

6. A method according to claim 1, wherein said chemiluminescent marker substance is an acridinium compound capable of undergoing a chemiluminescent reaction and of the general formula:

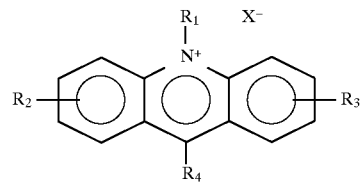

wherein $R_1$ is a moiety capable of being part of a quaternary nitrogen center selected from the group consisting of alkl, alkenyl, alkynyl, alkoxyl or aryl containing groups, $R_2$ and $R_3$ may be the same as $R_1$ or a hydroxyl, carboxyl, amino, substituted amino, or halide group, $R_4$ is a moiety whose chemical reactivity permits the compound to undergo chemilumnescent reaction selected from the group consisting of:

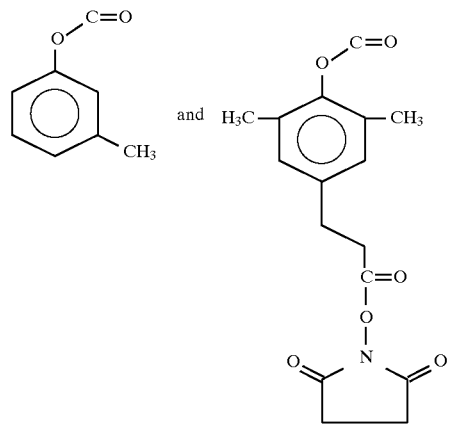

and $X^-$ is an anion.

7. A method according to claim 2, wherein said bulk liquid is selected from the group consisting of petroleum, diesel oil and lubricating oils.

8. A method of detecting subsequent dilution of a sample of bulk liquid which consists of introducing into an undiluted bulk liquid a known amount of a chemiluminescent marker substance, withdrawing a sample of said bulk liquid, initiating a chemiluminescent reaction in said sample, determining characteristics of said reaction, and comparing the characteristics of said reaction with those of a chemiluminescent reaction in the undiluted bulk liquid to determine the extent of dilution of said bulk liquid.

9. A method according to claim 8, wherein said bulk liquid is selected from the group consisting of petroleum, diesel oil, and lubricating oils.

10. A method according to claim 8, wherein said chemiluminescent marker substance is an acridinium compound capable of undergoing a chemiluminescent reaction and of the general formula:

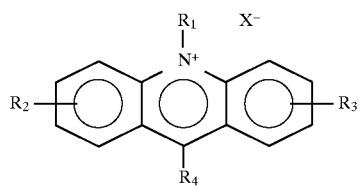

wherein $R_1$ is a moiety capable of being part of a quaternary nitrogen center selected from the group consisting of alky, alkenyl, alkynyl, alkoxyl or aryl containing groups, $R_2$ and $R_3$ may be the same as $R_1$ or a hydroxyl, carboxyl, amino, substituted amino, or halide group, $R_4$ is a moiety whose chemical reactivity permits the compound to undergo chemiluminescent reaction selected from the group consisting of:

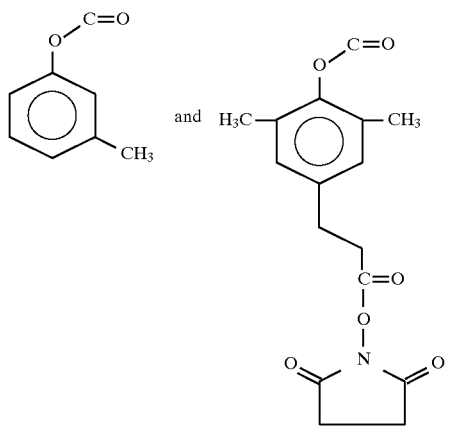

and $X^-$ is an anion.

11. A method of analyzing a bulk liquid to determine the presence or quantity of an additive present in the bulk liquid, said bulk liquid including a predetermined amount of a chemiluminescent marker substance indicating the presence of, or related to the quantity of, said additive, which method consists of withdrawing a sample of said bulk liquid to be identified or analyzed, initiating the chemiluminescent reaction in said sample and observing the characteristics of said reaction to determine the presence or the quantity of said additive.

12. A method according to claim 11, wherein said bulk liquid is selected from the group consisting of petroleum, diesel oil, and lubricating oils.

13. A method according to claim 11, wherein said chemiluminescent marker substance is an acridinium compound capable of undergoing a chemiluminescent reaction and of the general formula:

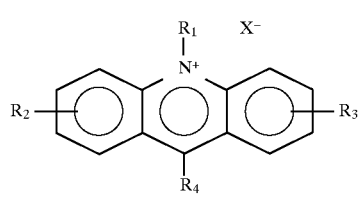

wherein $R_1$ is a moiety capable of being part of a quaternary nitrogen center selected from the group consisting of alkyl, alkenyl, alkynyl, alkoxyl or aryl containing groups, $R_2$ and $R_3$ may be the same as $R_1$ or a hydroxyl, carboxyl, amino, substituted amino, or halide group, $R_4$ is a moiety whose chemical reactivity permits the compound to undergo chemiluminescent reaction selected from the group consisting of:

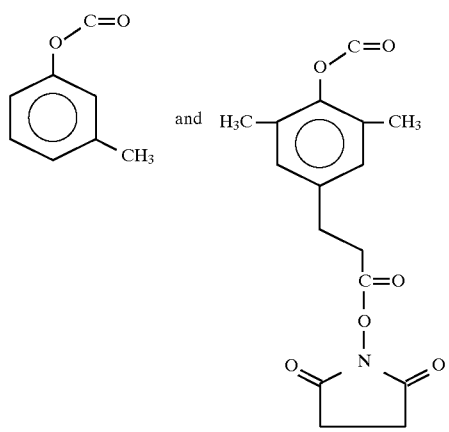

and $X^-$ is an anion.

* * * * *